United States Patent
Bauer

[11] Patent Number: 6,120,463
[45] Date of Patent: Sep. 19, 2000

[54] BIOPSY SURGICAL APPLIANCE

[75] Inventor: Alberto Bauer, Santo Domingo, Dominican Rep.

[73] Assignee: Allegiance Corporation, McGaw Park, Ill.

[21] Appl. No.: 09/044,811

[22] Filed: Mar. 20, 1998

[51] Int. Cl.[7] .................................................. A61B 10/00
[52] U.S. Cl. ...................... 600/567; 606/170; 606/167; 600/564
[58] Field of Search .................... 600/562, 564, 600/567, 568; 606/167, 181, 182, 184, 185, 170

[56] References Cited

U.S. PATENT DOCUMENTS

| | | | |
|---|---|---|---|
| 4,600,014 | 7/1986 | Beraha | 600/567 |
| 4,699,154 | 10/1987 | Lindgren | 600/567 |
| 4,907,599 | 3/1990 | Taylor | 600/567 |
| 4,917,100 | 4/1990 | Nottke | 600/567 |
| 4,944,308 | 7/1990 | Akerfeldt | 128/751 |
| 4,953,558 | 9/1990 | Akerfeldt | 600/567 |
| 4,958,625 | 9/1990 | Bates et al. | 128/754 |
| 5,025,797 | 6/1991 | Baran | 128/754 |
| 5,121,751 | 6/1992 | Panalletta | 128/754 |
| 5,125,413 | 6/1992 | Baran | 128/754 |
| 5,172,701 | 12/1992 | Leigh | 600/566 |
| 5,172,702 | 12/1992 | Leigh et al. | 600/567 |
| 5,243,994 | 9/1993 | Ranalletta | 600/567 |
| 5,368,045 | 11/1994 | Clement et al. | 600/567 |
| 5,400,798 | 3/1995 | Baran | 128/754 |
| 5,507,298 | 4/1996 | Schramm et al. | 600/567 |
| 5,538,010 | 7/1996 | Darr et al. | 600/567 |
| 5,595,185 | 1/1997 | Erlich | 128/754 |
| 5,617,874 | 4/1997 | Baran | 128/753 |
| 5,779,647 | 7/1998 | Chau et al. | 600/564 |
| 5,817,033 | 10/1998 | DeSantis et al. | 600/562 |
| 5,830,153 | 11/1998 | Kass | 600/567 |
| 5,876,354 | 3/1999 | Quinn et al. | 600/564 |

FOREIGN PATENT DOCUMENTS

WO 83/03343  10/1983  WIPO .

*Primary Examiner*—Cary O'Connor
*Assistant Examiner*—Charles Marmor, II
*Attorney, Agent, or Firm*—Paul E. Schaafsma

[57] ABSTRACT

A biopsy surgical appliance comprises a biopsy needle having a stylet (21) and a cannula (31), disposed coaxially along an axis (Y) and activated by a mechanical device with two slides (20, 30) which can slide longitudinally inside a shell (10, 50). The first slide (20) of the two slides (20, 30) has a "U" shape with tines (22a, 22b) oriented longitudinally and is moved longitudinally in a first operative environment, in which the central section (22c) of the "U" shape supports one component (21) of two components (21, 31) which constitute the biopsy needle (21, 31). The second slide (30) of the two slides (20, 30) has a head (32) which extends towards and beyond the axis (Y) without interfering with the first operative environment and is inserted freely between the tines (22a, 22b) of the first slide (20), and in which the head (32) supports the other component (31) of the two components (21, 31) which constitute the biopsy needs.

22 Claims, 9 Drawing Sheets

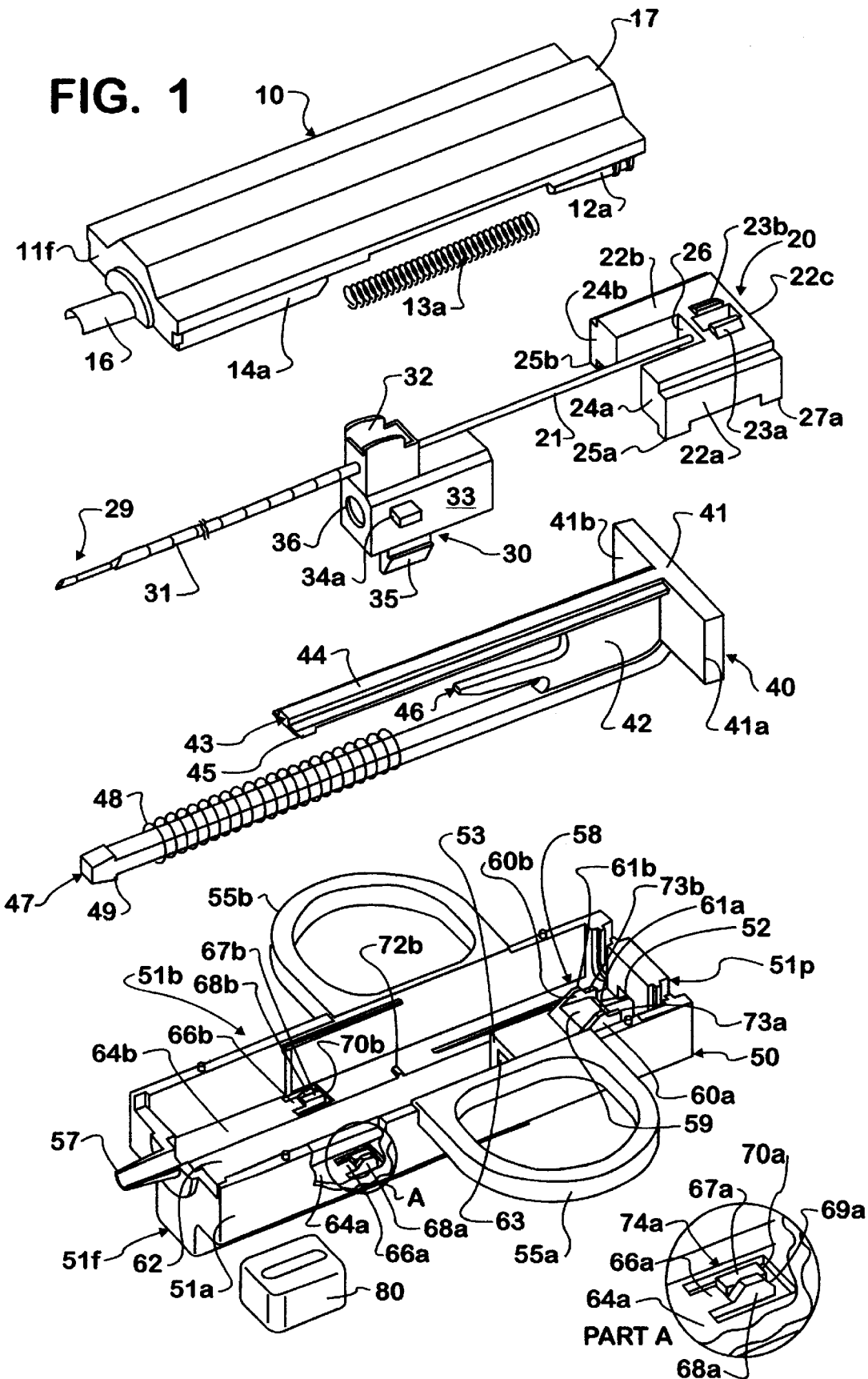

BIOPSY SURGICAL APPLIANCE

BACKGROUND OF THE INVENTION

FIELD OF THE INVENTION

The present invention relates to a biopsy surgical appliance.

Biopsy surgical appliances are commonly used to remove a sample of tissue from inside a living being.

At present, various biopsy surgical appliances are known, which include a biopsy needle, having a stylet and a cannula which extend coaxially, the rear portions of which are attached to a mechanical device which is disposed inside a shell, such that they can be activated automatically or semi-automatically.

In appliances of this type, the stylet consists of a thin probe, the front end of which is pointed and is preceded by a recess for accommodation of the sample to be collected. The cannula is fitted coaxially onto the stylet, slides axially relative to the stylet, and has a cutting front end which is designed to close the recess in the stylet.

The mechanical device has two slides which can slide longitudinally inside the shell. It also has resilient means designed to load the two slides resiliently and longitudinally, coupling/release means designed to retain the two slides in the armed position and to release them, loading means designed to bring the two slides into the armed position, and control means to release the two slides from their armed position. In order to use this appliance, it is first set in the armed position, and the front end of the biopsy needle is inserted in the vicinity of the tissue to be collected. Collection of a sample occurs by advancing in respective automatic or semi-automatic succession first the stylet and then the cannula.

By the way of example see patents U.S. Pat. No. 4,958, 625; EP-O,536.888; WO-91/01112 and U.S. Pat. No. 4,924, 787.

The known biopsy surgical appliances have some disadvantages.

A first disadvantage consists of the fact that they are very heavy, such that during use, the operator, must support the appliance continuously in order to eliminate undesirable advance movements and/or displacements caused by the action of the force of gravity.

A second disadvantage is caused by the fact that the appliances are complex to maneuver, and do not allow the operator to control and/or analyze and/or remove the sample easily after the needle has been extracted from the body of a patient.

A third disadvantage is the appliances are very costly, owing to a large number of components, and the complex structuring of the mechanical device which requires considerable assembly times.

SUMMARY OF THE INVENTION

The aim of the present invention is to eliminate the above-described disadvantages. The invention, which is characterized by the claims, solves the problem of the prior art.

The present invention is thus a biopsy surgical appliance, comprising a biopsy needle having two components, a stylet and a cannula, which are disposed coaxially with respect to each other and extend along an axis of the appliance. The appliance also has a shell to be grasped, in which the biopsy needle has a first free front portion which is designed to be inserted in a collection area, and a rear portion associated with a mechanical device for automation of the collection operations and is disposed inside the shell. The mechanical device has two slides which can slide longitudinally inside the shell, and are designed to support the rear portions of the stylet and the cannula, in which there are provided resilient means which are designed to load resiliently and longitudinally the two slides. The mechanical device also includes coupling/release means designed to retain the stylet and cannula in the armed position and release the two slides. The coupling/release means may include loading means designed to bring the two slides into the armed position. The coupling/release means, may also include control means to release the two slides from their armed position. The first slide has a "U" shape with tines which are oriented longitudinally and moved longitudinally in a first operative environment. A central section of the "U" shape supports the rear portion of one component of the two components which constitute the biopsy needle. The second slide has a head which extends towards and beyond the axis without interfering with the first operative environment of the first slide and is inserted freely between the tines of the first slide; the head supports the rear portion of the other component of the two components of the biopsy needle.

The present invention results in: an improvement in use, since it is lighter; an improvement in the post-collection operations, the purpose of which is to check and/or analyze and/or remove the sample; and a reduction in the manufacturing costs.

Further features and advantages of the present invention will become more apparent from the following detailed description of a preferred practical embodiment, provides here purely by way of non-limiting examples, with reference to the figures of the attached drawings.

BRIEF DESCRIPTION OF THE DRAWINGS

FIG. 1 is an exploded view of the components of the biopsy surgical appliance which is the subject of the present invention.

DESCRIPTION OF THE PREFERRED EMBODIMENT

Figure 1A:
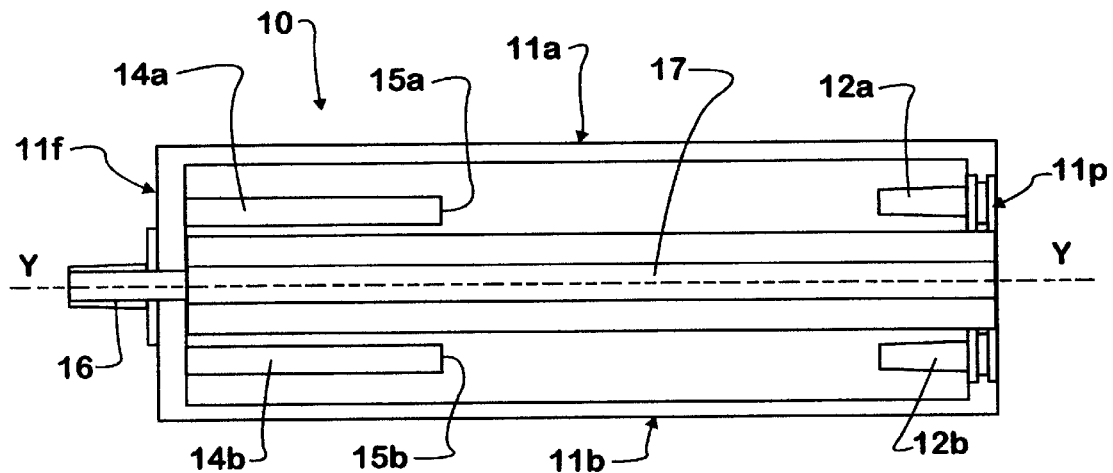
FIG. 1A is a view from below of the upper half-shell of the appliance.
Figure 1B:
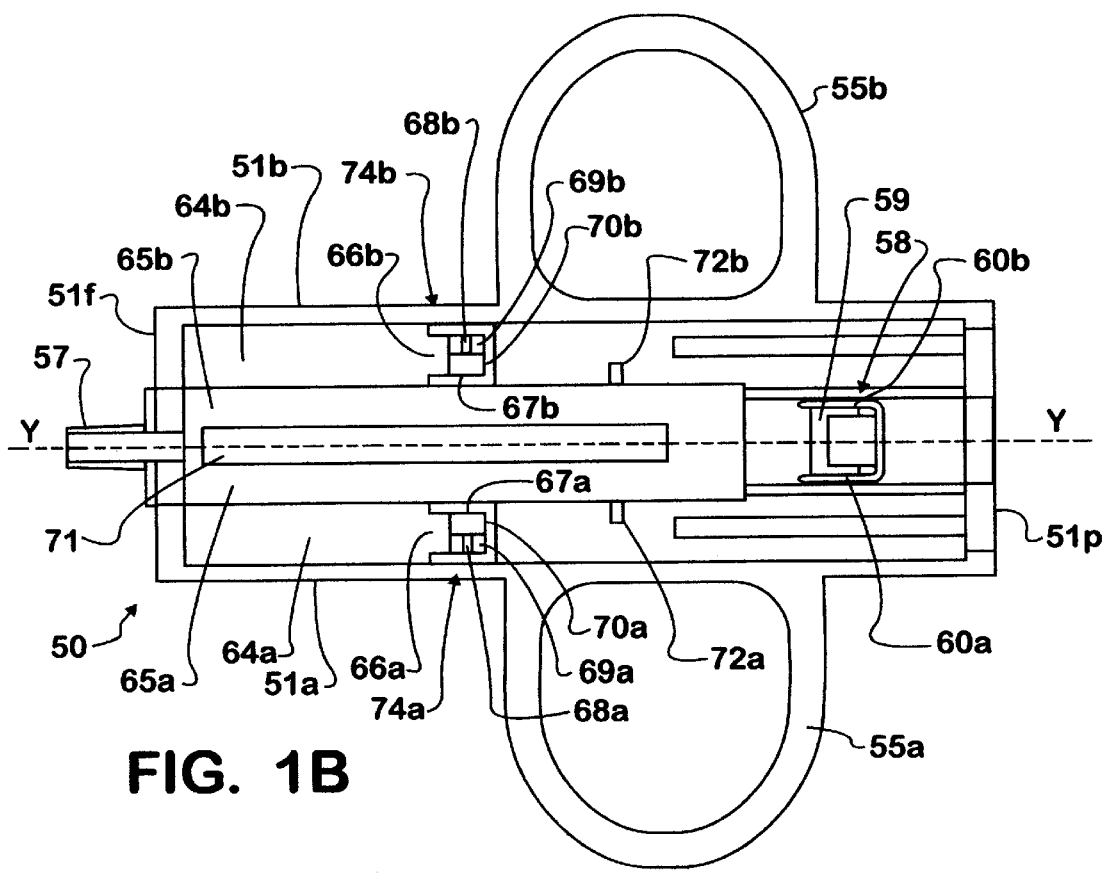
FIG. 1B is a plan view of the lower half-shell of the appliance.
Figure 1C:
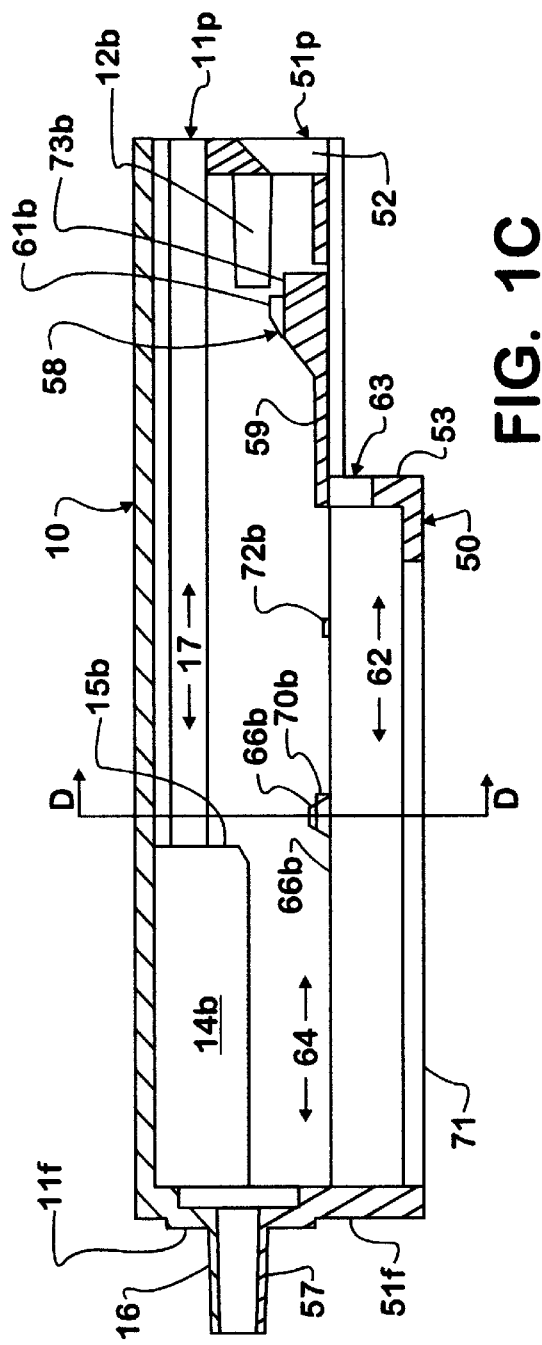
FIG. 1C is a cross-sectional view along the vertical median longitudinal plane, showing the two half-shells in FIGS. 1A and 1B joined.
Figure 1D:
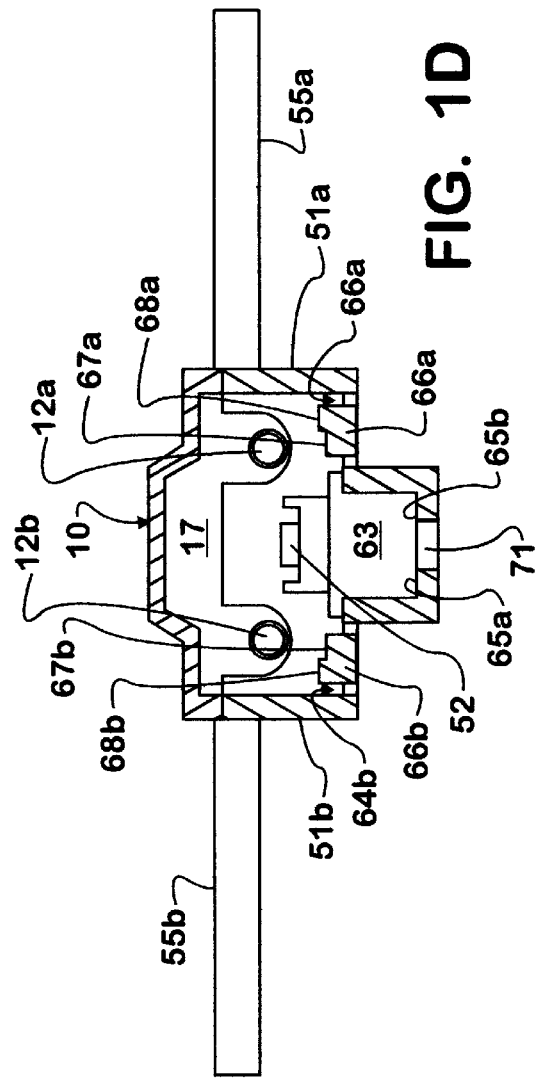
FIG. 1D is a view in cross-section along line D—D in FIG. 1C, showing the two half-shells in FIGS. 1A and 1B joined.

With reference to 1, 1A, 1B, 1C, 1D, 2, 2A and 2B, the biopsy surgical appliance is symmetrical relative to the vertical longitudinal median plane which is disposed along the longitudinal axis Y, and consists of various components. The components are: first, upper half-shell 10, with lateral retention walls 11a, 11b, a front wall 11f and rear wall 11p, in which the rear wall 11p has two pins 12a and 12b designed to bring the rear end of two respective springs 13a and 13b; the front wall 11f has at the front a pair of stop shoulders 14a and 14b with stop surfaces 15a, 15b, and a tube means 16 which allows a cannula 31 and a stylet 21 to emerge. In addition, a guide channel 17 extending longitudinally and centrally and is open at the rear is provided for reasons that are described below.

The device includes a first slide 20, designed to hold a stylet 21 which is provided with a recess 29 for accommodation of the sample collected. The first slide 20 has a horizontal "U"shape, the tines 22a, 22b of which are oriented longitudinally, and project towards the front of the appliance, and a central section 22c which has a stylet attached in the center.

In addition, the first slide 20 has: two upper teeth 23a, 23b; two front stop surfaces 24a and 24b; two front slider feet 25a and 25b which are disposed at the respective transverse ends, and have a calibrated transverse amplitude; two rear slider feet 27a and 27b (not shown); and a connection surface 26 which is disposed between the tines 22a and 22b.

Figure 4:
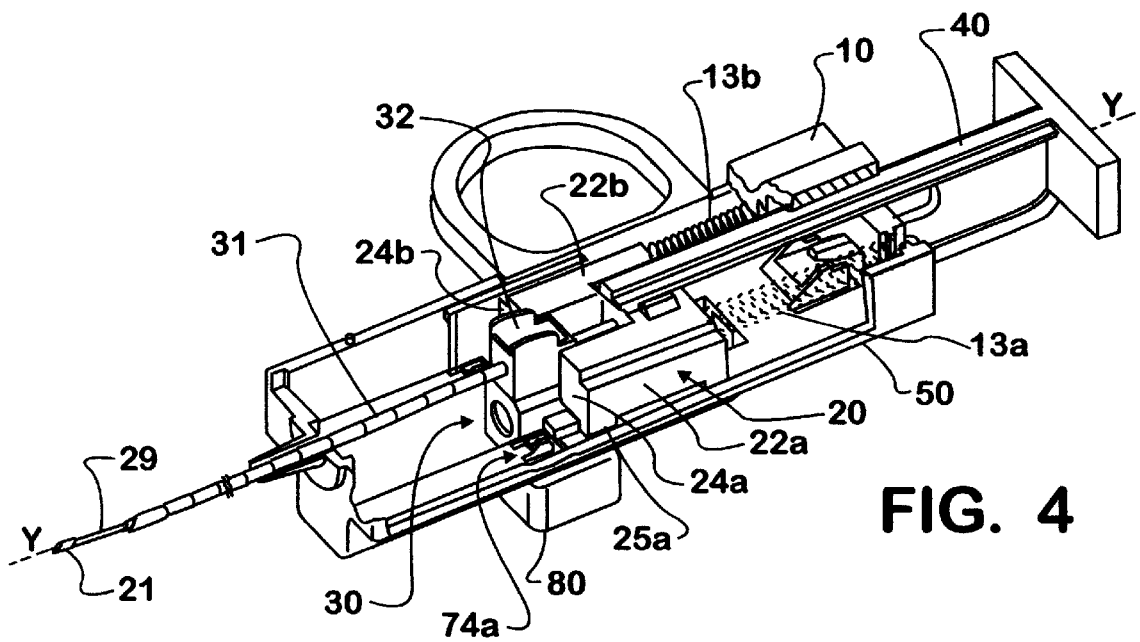
FIG. 4 is a perspective view illustrating the appliance in a position with the stylet advanced, with the upper half-shell in FIG. 1A partially removed.

A second slide 30, has a head 32 to which is attached the cannula 31, and has a shape such that it can be inserted in a sliding manner between the tines 22a and 22b of the first slide 20 (see also FIG. 4); a central body 33 which has fins 34a, 34b which project transversely; an extension 35 which projects from the exterior of the shell in order to be connected to a pawl 80, as described in greater detail below; and a longitudinal central through hole 36 which has a choke 37.

A three pronged activator component 40 is provided which is designed to set the two slides 20 and 30 in the armed position, and to activate them for the collection. The activator 40 has a grasping head 41 with grasping wings 41a and 41b; a central part 42; a first, upper branch 43 which has an upper longitudinal profile 44 which can slide inside the channel 17 of the first upper half-shell 10 and a drawing tooth 45 which can engage the teeth 23a, 23b of the first slide 20; and a second, short intermediate branch 46 which has a wedge-shaped tapered end; and a third branch 47, which is designed to bring a spring 48 which is fitted onto the third branch 47, and has an engagement head 49 at its free end.

A second, lower half-shell 50 is also provided which has lateral retention walls 51a, 51b, a front wall 51f and a rear wall 51p, in which the rear wall 51p has a square through-hole 52; the two lateral walls 51a, 51b have two outer rings 55a, 55b which are designed to act as grasping components for the operator's fingers; and the front wall 51f has a tube means 57 which is designed to permit sliding of the needle for biopsy.

In its rear part, the base of the second lower half-shell 50 has a first automatic coupling 58, which consists of a flexible tab 59 which has two lateral shoulders 60a, 60b, which form two retention teeth 61a, 61b and two support projections 73a, 73b. Below the flexible tab 59, towards the front of the appliance, there is a longitudinal channel 62 which is open at the top, the rear wall 53 of which has a through-hole 63.

The second half-shell 50 forms two lower sliding planes, the first 64a, 64b, which are disposed at the side and at the level of the top of the channel 62; and the second 65a, 65b, on the base of the central channel 62, in which this latter plane 65a, 65b has a longitudinal through-slot 71, for the reasons which will be described below.

The two sliding planes 64a, 64b have respective second coupling/release means 74a, 74b, each of which consists of a flexible tab 66a, 66b which has two sets of projections 67a, 67b, 68a, and 68b, in which the projections 67a, 67b have coupling teeth 70a, 70b, and in which the projections 68a, 68b have inclined planes 69a, 69b which are oriented from the exterior towards the interior, and from the rear towards the front of the shell 50, for the reasons described below. In addition, respective intermediate stop teeth 72a, 72b are provided along the sliding planes 64a, 64b.

Figure 2:
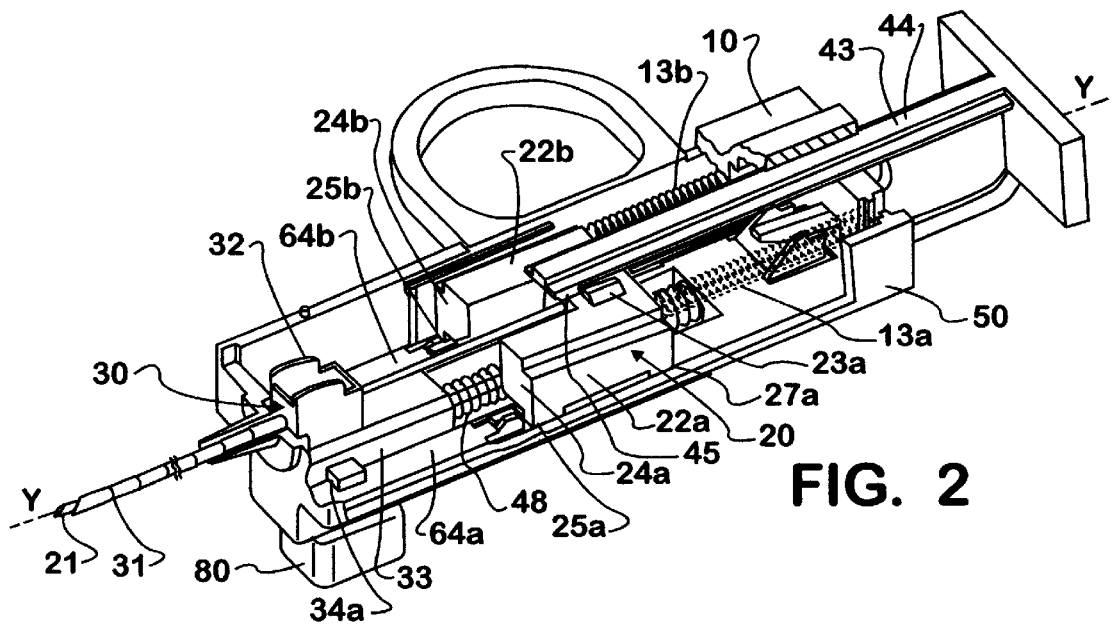
FIG. 2 is a perspective view showing the appliance in a rest position, with the upper half-shell in FIG. 1A partially removed.
Figure 2A:
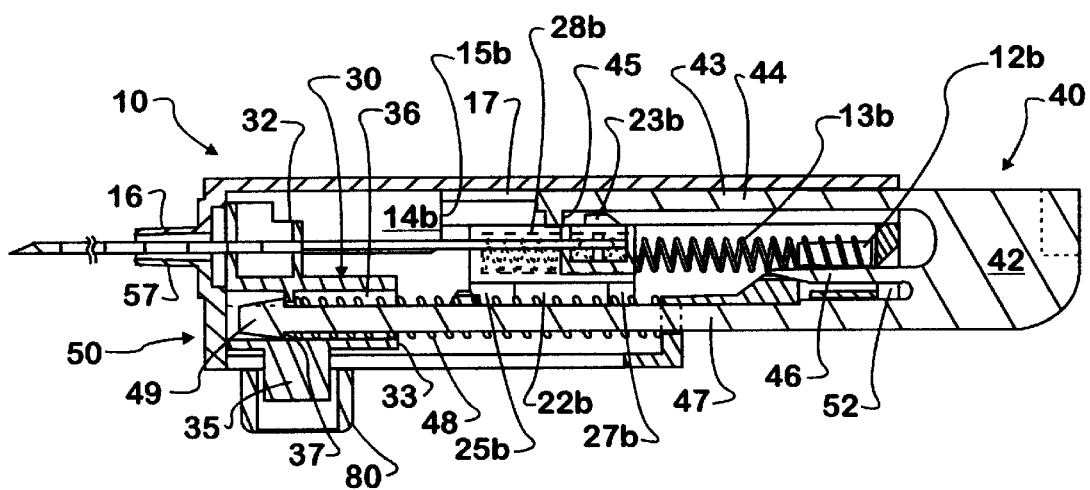
FIG. 2A is a cross-sectional view along the vertical median longitudinal plane of the appliance illustrated in FIG. 2.
Figure 2B:
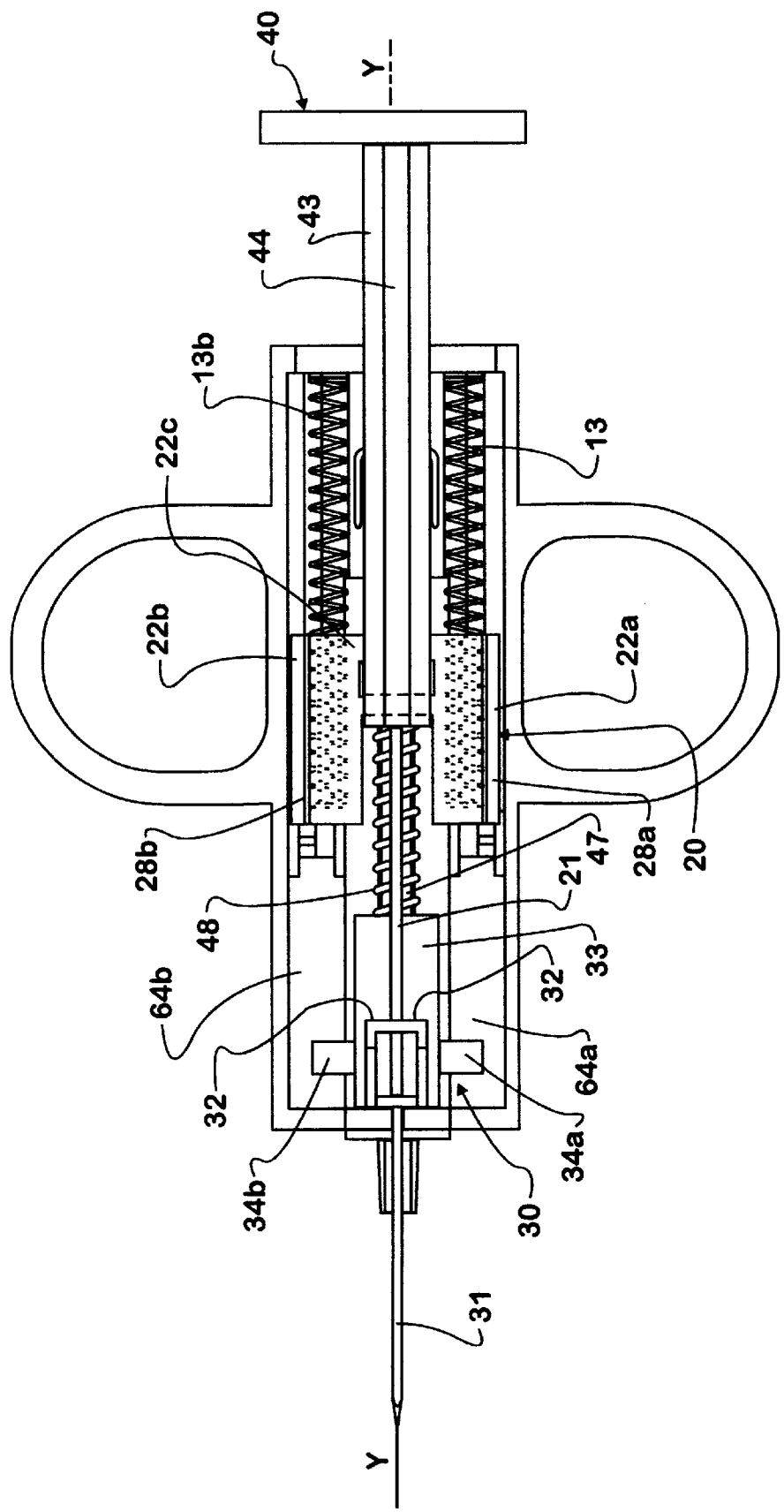
FIG. 2B is a schematic plan view of the appliance illustrated in FIG. 2.

With reference to FIGS. 2, 2A and 2B, when the various components are assembled and are disposed inside the upper half-shell 10 and the lower half-shell 50, the first slide 20 has its own feet 25a, 25b, 27a, 27b supported in a sliding manner on the sliding planes 64a, 64b. The first slide 20 is also thrust forwards by springs 13a, 13b which have one end fitted onto the pins 12a, 12b of the half-shell 10, and the other end accommodated in blind holes 28a, 28b which are oriented axially, and are provided in the rear part of the first slide.

The second slide 30 is disposed with its lower part 33 partially inside the sliding channel 62, and has its fins 34a, 34b supported in a sliding manner on the sliding planes 64a, 64b.

The activator 40 is disposed at the rear and has: the first branch 43, with the corresponding upper longitudinal profile 44, inserted longitudinally in a guided sliding manner along the channel 17 of the first half-shell 10, with the entrainment tooth 45 in the vicinity of the teeth 23a 23b of the first slide 20. The second branch 46, is inserted longitudinally in a sliding manner through the aperture 52, with its wedge-shaped free end inserted between the shoulders 60a, 60b of the first flexible coupling 58. The third branch 47 is inserted longitudinally in a sliding manner through the aperture 63, with its head 49 disposed beyond the choke 37 provided in the hole 36.

The spring 48 is fitted onto the branch 47. The spring 48 has its front part partially disposed inside the hole 36, and its opposite ends disposed against the rear surface of the choke 37 and against the front surface of the rear wall of the channel 62, in order to thrust the second slide 30 forwards.

In order to set the appliance in the armed position, the activator 40 is drawn rearwards, which action draws the first slide 20 rearwards by the interception of the tooth 45 against the teeth 23a 23b, and draws the second slide 30 rearwards by interception of the head 49 against the front wall of the choke 37.

Figure 3:
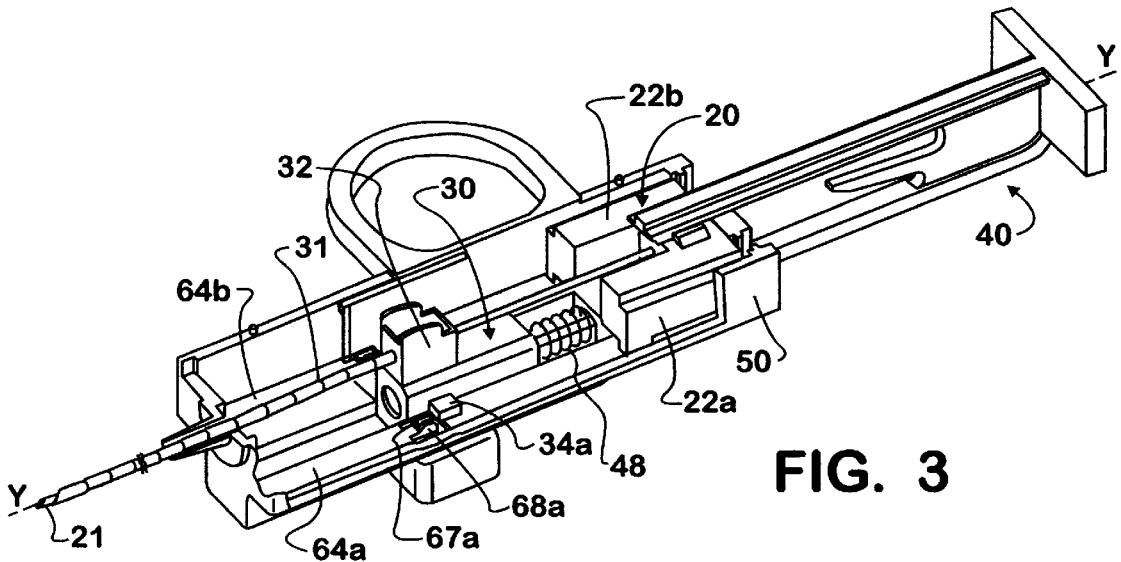
FIG. 3 is a perspective view illustrating the appliance in an armed position, with the upper half-shell in FIG. 1A partially removed.
Figure 3A:
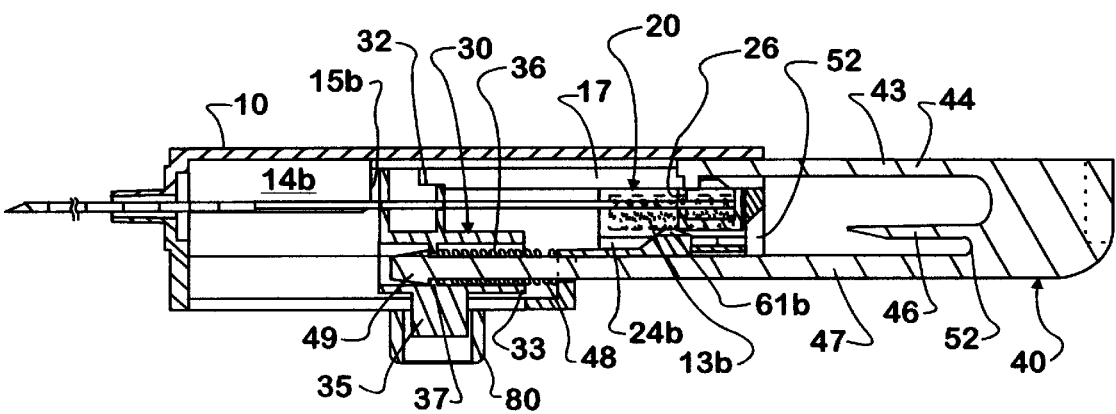
FIG. 3A is a cross-sectional view along the vertical median longitudinal plane, of the appliance illustrated in FIG. 3.

FIGS. 3 and 3A illustrate the configuration of the appliance after the action of loading or arming. In this position, the slide 20 is coupled in the armed position, with the springs 13a, 13b compressed, since the coupling teeth 61a, 61b are coupling the front wall 26 of the first slide 20. The slide 30 is also coupled in the armed position with the spring 48 compressed, since the coupling teeth 70a, 70b are coupling the front surface of the fins 34a, 34b.

In this configuration, the biopsy needle is inserted in the patient in order to position it in the vicinity of the area where the collection is to be carried out.

Figure 4A:
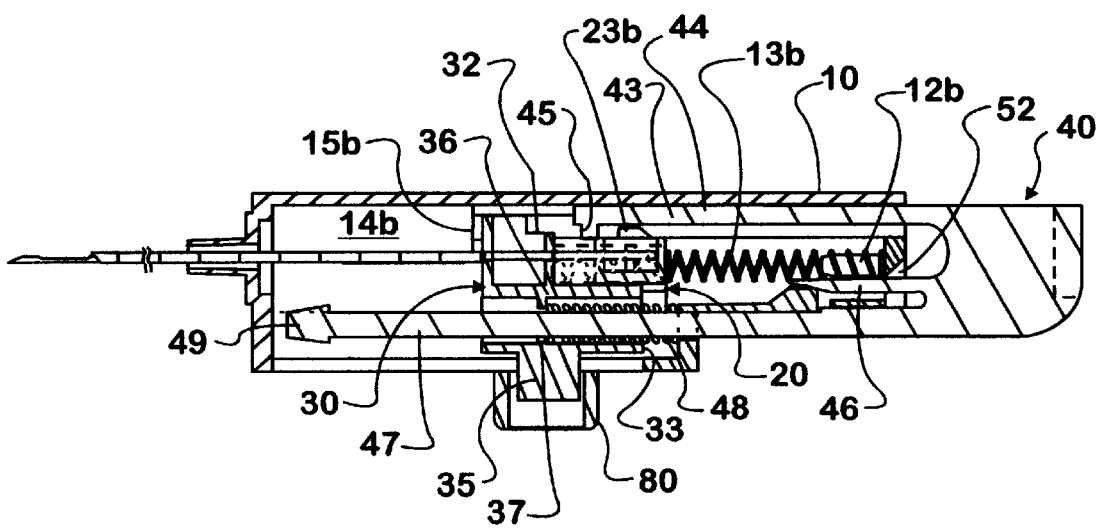
FIG. 4A is a cross-sectional view along the vertical medial longitudinal plane of the appliance illustrated in FIG. 4.

When the needle is in the correct position (see also FIGS. 4 and 4A), the operator advances the activator 40 and the branch 46 enters the upper half-shell 10 via the aperture 52.

Further advance of the activator 40 gives rise to infra-positioning of the wedge-shaped end of the branch 46 between the flexible tab 59 and the central section 22c of the first "U"-shaped slide 20. There is a consequent displacement towards the exterior of the free end of the tab 59 and of the corresponding coupling teeth 61a, 61b, until release or uncoupling takes place of the first slide 20, which, thrust by the springs 13a, 13b and sliding with its own feet 25a, 27a, and 25b, 27b on the respective sliding planes 64a, 64b, moves forwards, advancing the tip of the stylet 21 which perforates the tissue to be collected.

Figure 5:
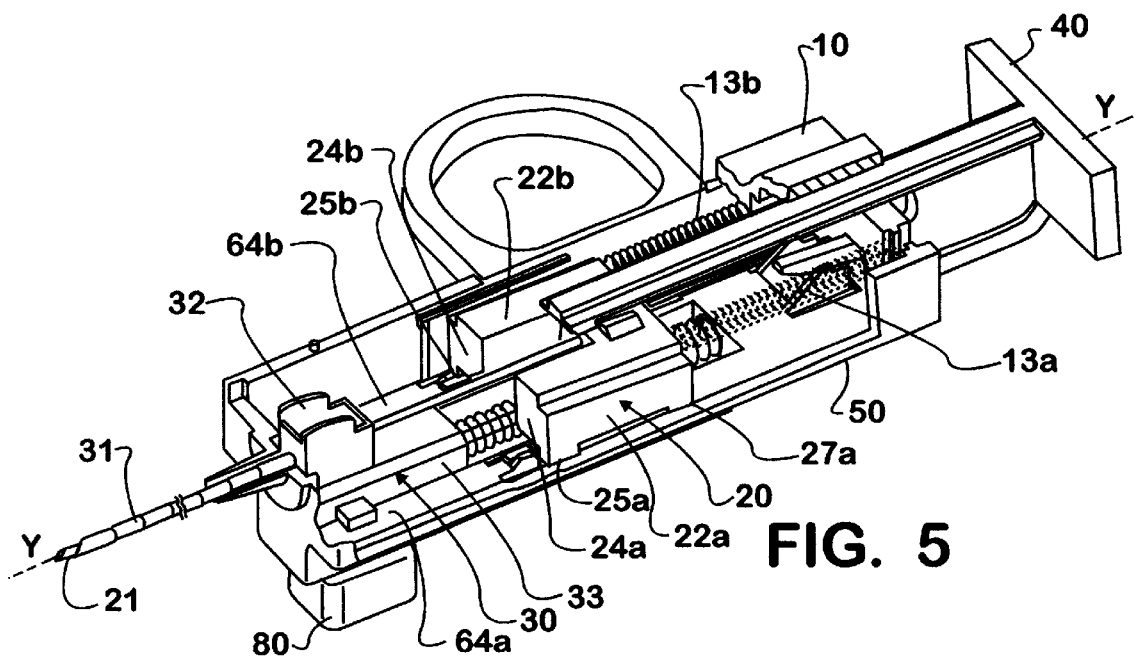
FIG. 5 is a perspective view illustrating the appliance in a specific cross-sectional position, with the upper half-shell in FIG. 1A partially removed.
Figure 5A:
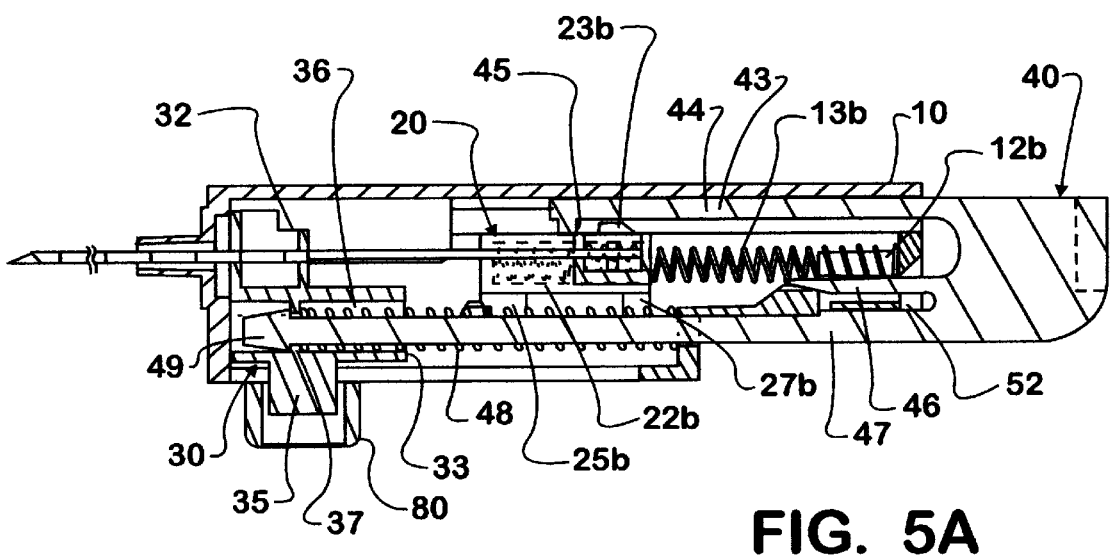
FIG. 5A is a cross-sectional view along the vertical medial longitudinal plane of the appliance illustrated in FIG. 5.

Referring now to FIGS. 5 and 5A, owing to their transverse arrangement and transverse amplitude, when they move forward, the front feet 25a, 25b of the first slide 20 pass to the side of the fins 34a 34b and to the side of the coupling teeth 70a 70b. Before the first slide 20 ends its forward path, which terminates when the front surfaces 24a, 24b abut the rear surfaces 15a, 15b of the shoulders 14a, 14b, and the front surface of the rear feet 27a, 27b abuts the rear surfaces of the intermediate stop teeth 72a, 72b, the front feet 25a, 25b engage with the respective inclined planes 69a, 69b of the projections 68a, 68b. This engagement gives rise to flexure towards the exterior of the free ends of the flexible tabs 66a, 66b, with consequent displacement towards the exterior of the coupling teeth 70a, 70b, and corresponding release or uncoupling of the slide 30. The slide 30, thrust by the spring 48, begins its path of advance towards the front, advancing the cutting end of the cannula 31, which closes the recess 29, isolating a piece of tissue which is accommodated in the recess 29 from the remainder of the surrounding tissue.

With reference to the end of travel of the first slide 20, caused by the rear feet 27a, 27b meeting the intermediate stop teeth 72a, 72b, it must be pointed out that the rear feet 27a, 27b have a greater transverse amplitude than the front feet 25a, 25b. While the first slide 20 is being advanced by the springs 13a, 13b, owing to their smaller transverse amplitude the front feet 25a, 25b move to the side of the intermediate stop teeth 72a, 72b, whereas owing to their greater transverse amplitude the rear feet 27a, 27b interfere with the same intermediate stop teeth 72a, 72b, thus activating the end of travel function.

Figure 6:
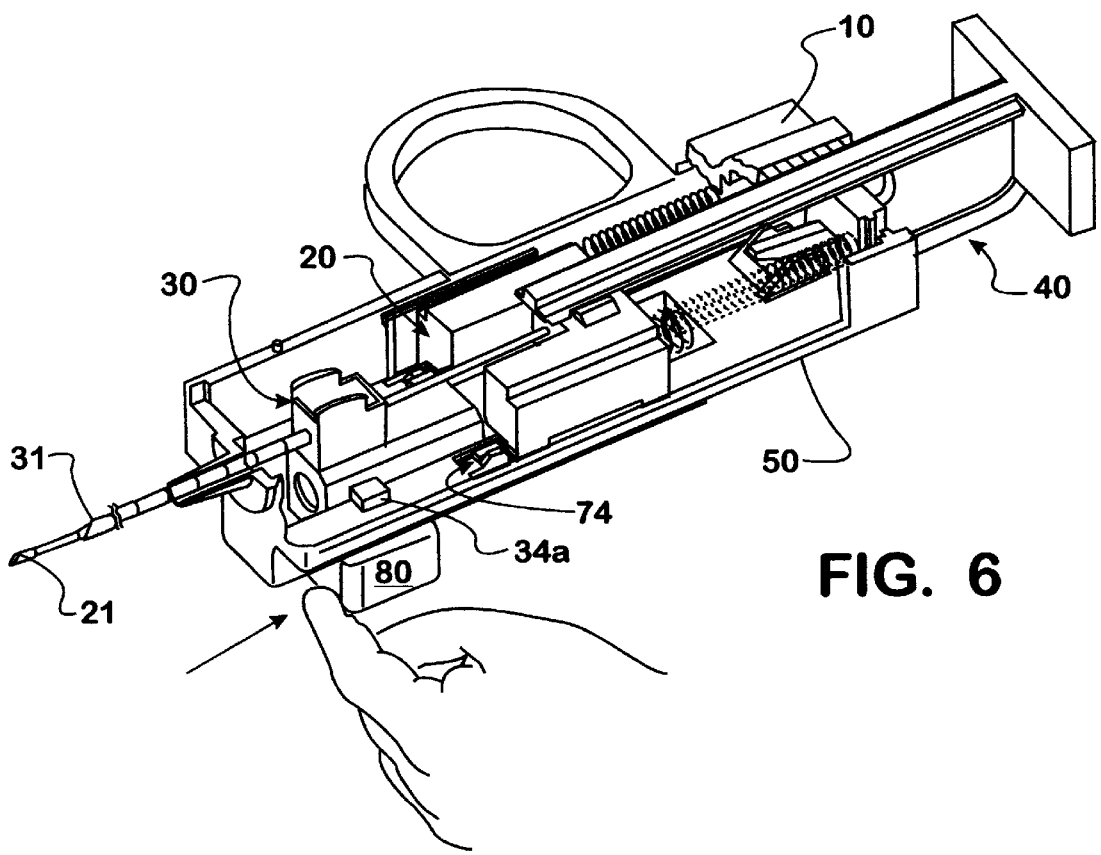
FIG. 6 is a perspective view illustrating the appliance in a specific position which is designed to show the sample taken, with the upper half-shell in FIG. 1A partially removed.

When the sample has been isolated, the biopsy needle can be extracted from the body of the patient. If the operator wishes to inspect immediately the sample collected, the operator can press the pawl 80 as illustrated in FIG. 6, when the movement rearwards has been completed. The operator then can easily and immediately uncover the recess 29 of the stylet 21, and expose the corresponding sample accommodated there, since rearward movement of the pawl 80, which is associated with the second slide 30 by means of the projection 35, gives rise to rearward movement of the tube 31 which is attached to the second slide 30.

More specifically, uncovering the recess 29, with consequent exposure of the sample, can be of two types. The uncovering can be temporary, if the rearward displacement of the pawl 80 has a path such that it does not take the finds 34a, 34b of the second slide 30 beyond the coupling teeth 70a, 70b. The uncovering can be permanent, if the rearward displacement of the pawl 80 has a path such that it takes the fins 34a, 34b of the second slide 30 beyond the rear end of the coupling teeth 70a, 70b, with consequent coupling.

The first, temporary configuration can be used for example in order to examine whether the collection has taken place satisfactorily. The second, permanent configuration can be used for example in order to remove the sample obtained, easily from the recess 29.

With reference to the specific configuration of the two slides 20 and 30, in which the head 32 of the second slide 30 is designed to be inserted between the tines 22a, 22b of the first slide 20, it is apparent that this functional arrangement permits reduction of the length of the upper half-shell 10 and the lower half-shell 50, compared with the previous embodiments in which the slides were disposed one behind the other. The arrangement of the present invention provides a consequent reduction of the weight of the upper half-shell 10 and the lower half-shell 50.

When the biopsy needle has been extracted from the patient, with particular reference to the slide 30 of the cannula 31, to the projection 35 which emerges from the lower half-shell 50, and to the pawl 80, it is apparent that an operator can quickly and easily expose, and thus check the sample obtained, by means of simple and natural displacement rearwards of the pawl 80.

In addition, the operator can choose whether to uncover the collection aperture 29 in order to examine the sample, and then re-close or to uncover the aperture 29 permanently.

Finally, with particular reference to the structure of the activating device, the components of the present invention are decidedly small and lighter than the previous embodiments, with consequent reduction of the costs of production and weight of the biopsy surgical appliance.

Figure 7:
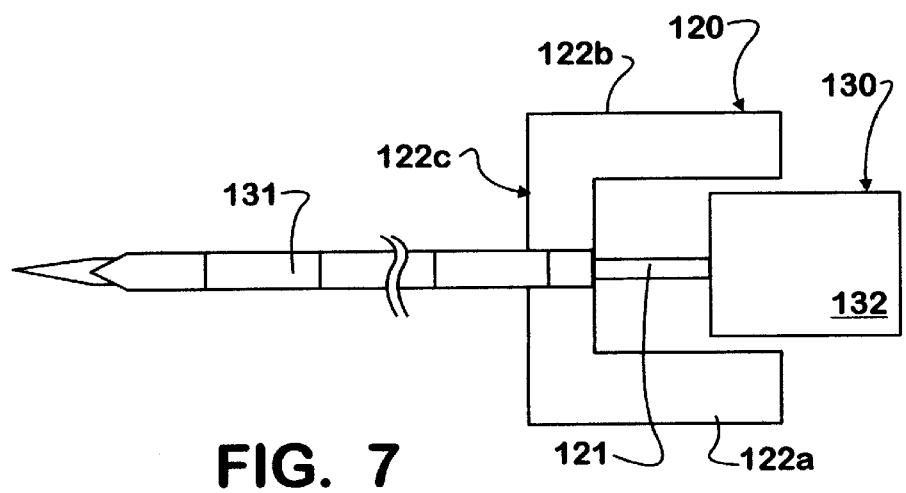
FIG. 7 illustrates schematically an alternative embodiment of the present invention.

FIG. 7 illustrates an alternative embodiment of the present invention, which is equivalent to that described above.

In this embodiment, a first slide 120 in the shape of a "U", with tines 122a and 122b, and a central section 122c, supports the rear portion of a cannula 131, and a slide 130 with a head 132, in which the latter has a shape such that is can be inserted between the tines 122a, 122b of the "U", and supports a stylet 121.

The predetermined objectives are also obtained by means of this alternative embodiment.

The description of the biopsy surgical appliance which is the subject of the present invention, is provided purely by way of non-limiting example, and it is thus apparent that there can be made to it all modifications or variants which are suggested by practice or by its utilization or use, provided that these are within the context of the following claims.

What is claimed is:

1. An automated surgical appliance for collecting a sample, the surgical appliance comprising:
   a shell;
   a projection moveably disposed in the shell;
   a biopsy needle disposed in the shell, the biopsy needle having a stylet and a cannula, both the stylet and the cannula adapted for insertion into a collection area for collecting the sample, the cannula operatively associated with the projection; and a pawl connected to the projection;

wherein the cannula may be moved by movement of the pawl to expose the stylet and any sample contained therein, further wherein the cannula may be moved by movement of the pawl to cover the stylet and any sample contained therein.

2. The biopsy surgical appliance of claim 1, further comprising:

a slide connected to the cannula with the projection connected to the slide such that the projection projects outside the shell, the projection connected to the pawl, wherein movement of the pawl produces movement of the slide and thereby the movement of the cannula.

3. The biopsy surgical appliance of claim 1, further comprising:

a first slide connected to the cannula;

a second slide connected to the stylet;

a first coupling/release mechanism operatively associated with the first slide;

a second coupling/release mechanism operatively associated with the second slide; and a control mechanism operatively associated with the first coupling/release mechanism wherein the control mechanism releases the first slide from an armed position resulting in a movement of the first slide in the shell such that the movement of the first slide actuates the second coupling/release mechanism thereby releasing the second slide from an armed position.

4. The biopsy surgical appliance of claim 3, wherein the first coupling/release mechanism comprises a flexible tab operatively associated with a plurality of coupling teeth.

5. The biopsy surgical appliance of claim 3, wherein the second coupling/release mechanism comprises:

a plurality of flexible tabs disposed in the shell;

a plurality of coupling teeth, such that a coupling tooth is disposed on each of the flexible tabs; and a plurality of fins disposed on the second slide such that a fin may engage a coupling tooth when the stylet is placed into an armed position;

wherein the flexible tab may flex to release the coupling tooth from engagement with the fin and thereby release the stylet from an armed position.

6. An automated surgical appliance for collecting samples, the surgical appliance comprising:

a shell;

a biopsy needle disposed in the shell, the biopsy needle having a stylet and a cannula, both the stylet and the cannula adapted for insertion into a collection area for collecting a sample;

an activator including a first branch operatively associated with the stylet, a second branch operatively associated with the shell, and a third branch operatively associated with the cannula, such that the activator may arm both the cannula and the stylet simultaneously.

7. The biopsy surgical appliance of claim 6, further comprising:

a slide connected to the cannula;

an extension connected to the slide such that the extension projects outside the shell, the extension connected to a pawl, wherein movement of the pawl produces movement of the slide and thereby movement of the cannula.

8. The biopsy surgical appliance of claim 6, further comprising:

a first slide connected to the cannula;

a second slide connected to the stylet;

a first coupling/release mechanism operatively associated with the first slide;

a second coupling/release mechanism operatively associated with the second slide; and a control mechanism operatively associated with the first coupling/release mechanism wherein the control mechanism releases the first slide from an armed position resulting in a movement of the first slide in the shell such that the movement of the first slide actuates the second coupling/release mechanism thereby releasing the second slide from an armed position.

9. The biopsy surgical appliance of claim 8, wherein the first coupling/release mechanism comprises a flexible tab operatively associated with a plurality of coupling teeth.

10. The biopsy surgical appliance of claim 8, wherein the second coupling/release mechanism comprises:

a plurality of flexible tabs disposed in the shell;

a plurality of coupling teeth, such that a coupling tooth is disposed on each of the flexible tabs; and a plurality of fins disposed on the second slide such that a fin may engage a coupling tooth when the stylet is placed into an armed position;

wherein the flexible tab may flex to release the coupling tooth from engagement with the fin and thereby release the stylet from an armed position.

11. An automated surgical appliance for collecting samples, the surgical appliance comprising:

a shell;

a biopsy needle disposed in the shell, the biopsy needle having a stylet and a cannula, both the stylet and the cannula adapted for insertion into a collection area for collecting a sample;

a first slide connected to the cannula;

a second slide connected to the stylet;

an activator slidably disposed in the shell, the activator including a first branch connected to the second slide, a second branch operatively associated with the shell, and a third branch connected to the first slide, such that when the activator is moved in the shell the first slide may move coaxially with respect to the second slide.

12. The automated surgical appliance of claim 11, further comprising:

a first coupling/release mechanism operatively associated with the first slide;

a second coupling/release mechanism operatively associated with the second slide; and a control mechanism operatively associated with the first coupling/release mechanism wherein the control mechanism releases the first slide from an armed position resulting in a movement of the first slide in the shell such that the movement of the first slide actuates the second coupling/release mechanism thereby releasing the second slide from an armed position.

13. The biopsy surgical appliance of claim 12, wherein the first coupling/release mechanism comprises a flexible tab operatively associated with a plurality of coupling teeth.

14. The biopsy surgical appliance of claim 12, wherein the second coupling/release mechanism comprises:

a plurality of flexible tabs disposed in the shell;

a plurality of coupling teeth, such that a coupling tooth is disposed on each of the flexible tabs; and a plurality of fins disposed on the second slide such that a fin may engage a coupling tooth when the stylet is placed into an armed position;

wherein the flexible tab may flex to release the coupling tooth from engagement with the fin and thereby release the stylet from an armed position.

15. An automated surgical appliance for collecting samples, the surgical appliance comprising:
- a shell;
- a biopsy needle disposed in the shell, the biopsy needle having a stylet and a cannula, both the stylet and the cannula adapted for insertion into a collection area for collecting a sample;
- a first slide connected to the cannula;
- a second slide connected to the stylet;
- an activator including a first branch connected to the second slide, a second branch operatively associated with the shell, and a third branch connected to the first slide;
- a first resilient member and a second resilient member disposed in the shell and operatively associated with the first slide such that the first resilient member and the second resilient member are held in compression when the cannula is placed in an armed position; and
- a third resilient member disposed on the third branch and operatively associated with the second slide such that the third resilient member is held in compression when the stylet is placed in an armed position.

16. The automated surgical appliance of claim 15, wherein the first slide and the second slide may move coaxially within the shell.

17. The automated surgical appliance of claim 15, wherein the first resilient member is a spring.

18. The automated surgical appliance of claim 15, wherein the second resilient member is a spring.

19. The automated surgical appliance of claim 15, wherein the third resilient member is a spring.

20. The automated surgical appliance of claim 15, further comprising:
- a first coupling/release mechanism operatively associated with the first slide;
- a second coupling/release mechanism operatively associated with the second slide; and
- a control mechanism operatively associated with the first coupling/release mechanism wherein the control mechanism releases the first slide from an armed position resulting in a movement of the first slide in the shell such that the movement of the first slide actuates the second coupling/release mechanism thereby releasing the second slide from an armed position.

21. The biopsy surgical appliance of claim 20, wherein the first coupling/release mechanism comprises a flexible tab operatively associated with a plurality of coupling teeth.

22. The biopsy surgical appliance of claim 20, wherein the second coupling/release mechanism comprises:
- a plurality of flexible tabs disposed in the shell;
- a plurality of coupling teeth, such that a coupling tooth is disposed on each of the flexible tabs; and
- a plurality of fins disposed on the second slide such that a fin may engage a coupling tooth when the stylet is placed into an armed position;

wherein the flexible tab may flex to release the coupling tooth from engagement with the fin and thereby release the stylet from an armed position.

* * * * *